United States Patent [19]

Decker et al.

[11] Patent Number: 4,976,137

[45] Date of Patent: Dec. 11, 1990

[54] CHEMICAL MIXING AND DISPENSING SYSTEM

[75] Inventors: James D. Decker, Apple Valley; Wendell D. Burch, Elko; Daniel F. Brady, Eagan; Gary W. Hinzman, St. Paul, all of Minn.; Edward P. Kromrey, Osceola, Wis.; Katherine M. Sanville, White Bear Lake, Minn.; Donald R. Southworth, Inver Grove Heights, Minn.; Mark S. Chace, New Brighton, Minn.; Perry M. Peloquin, St. Paul, Minn.

[73] Assignee: Ecolab Inc., St. Paul, Minn.

[21] Appl. No.: 294,290

[22] Filed: Jan. 6, 1989

[51] Int. Cl.[5] .......... G01N 33/00

[52] U.S. Cl. .......... 73/53; 222/23

[58] Field of Search .......... 73/53, 3; 222/23, 52, 222/55, 56, 58, 129.1, 129.2

[56] References Cited

U.S. PATENT DOCUMENTS

| | | | |
|---|---|---|---|
| 2,823,833 | 2/1958 | Bauerlein | 222/129.2 |
| 2,913,893 | 11/1959 | Mathews et al. | 68/18 |
| 2,955,726 | 10/1960 | Feldman et al. . | |
| 2,978,951 | 4/1961 | Christie | 73/53 X |
| 3,268,119 | 8/1966 | Kopera | 222/129.1 |
| 3,342,199 | 9/1967 | McEvoy | 137/88 |
| 3,529,529 | 9/1970 | Schumacher | 95/89 |
| 3,532,102 | 10/1970 | Glassey | 137/91 |
| 3,557,608 | 1/1971 | Molof | 73/53 |
| 3,559,663 | 2/1971 | Every | 137/5 |
| 3,611,790 | 10/1971 | Brouwer et al. | 73/61.1 |
| 3,698,238 | 10/1972 | Wall et al. | 73/53 |
| 3,701,609 | 10/1972 | Bailey | 210/198 |
| 3,723,712 | 3/1973 | Kromline, Sr. et al. . | |
| 3,815,620 | 6/1974 | Dziomba et al. | 137/90 |
| 3,877,682 | 4/1975 | Moss . | |
| 4,019,653 | 4/1977 | Scherer et al. | 222/52 X |
| 4,474,476 | 10/1984 | Thomsen | 366/152 |
| 4,538,222 | 8/1985 | Crain et al. | 364/172 |
| 4,648,043 | 3/1987 | O'Leary | 364/510 |
| 4,691,850 | 9/1987 | Kirschmann et al. | 222/642 |
| 4,733,798 | 3/1988 | Brady et al. | 222/23 |

FOREIGN PATENT DOCUMENTS

| | | | |
|---|---|---|---|
| 0196398 | 10/1986 | European Pat. Off. | 222/23 |
| 1383935 | 2/1975 | United Kingdom . | |

OTHER PUBLICATIONS

"Formulator Dispensing System", Ecolab Inc., Formulator Installation and Operation Manual.

*Primary Examiner*—Hezron E. Williams
*Assistant Examiner*—Joseph W. Roskos
*Attorney, Agent, or Firm*—Merchant, Gould, Smith, Edell, Welter & Schmidt

[57] ABSTRACT

An apparatus and method for mixing and dispensing chemical solutions are disclosed. The blending unit (11) includes a manifold (38) having a plurality of chemical inlet ports (39), a water inlet port (45), and an outlet port (46). A plurality of pumps (43) and valves (41) are associated with the chemical inlet ports (39). The outlet port (46) is connected to dispensing outlets (25, 29) for dispensing the chemical solutions and water into a container 16. The apparatus (10) also includes a quality control systems, including a conductivity cell (50), a weight measurement station (26), and a volume flow measurement device. The apparatus (10) also includes an electronic control unit (70) associated with the pumps (43) and valves (41) to operate them in response to a pre-selected volume, sequential combination and concentration of chemicals.

25 Claims, 6 Drawing Sheets

CHEMICAL MIXING AND DISPENSING SYSTEM

FIELD OF THE INVENTION

The present invention relates generally to an apparatus and method for combining a plurality of chemical solutions, and more particularly to an apparatus and method for automatically dispensing accurate amounts of a plurality of chemical solutions so as to produce a variety of liquid cleaning products.

BACKGROUND OF THE INVENTION

Chemicals such as those used in cleaning have typically been provided in several fashions. First, such chemicals can be provided in concentrations and combinations of ingredients appropriate to end use. The problem with this method of distribution is the large number of separate mixtures which are appropriate for various uses, as well as the large amount of volume and weight required for storing and shipping of these chemicals due to the substantial amount of water which is present in any end use chemical.

One method of solving the volume and weight problem is to provide the chemical in concentrated form, thereby allowing the end user to appropriately dilute the solution as desired. While this approach may seem attractive, such dilution can cause problems in that it is hard to get the appropriate exact dilutions required for various applications, such as cleaning. Solutions which are too concentrated or too dilute may be equally unsuitable.

Chemical processing plants mix cleaning chemicals on a large scale, but the machinery used is quite expensive and complicated. The conventional method for producing relatively large quantities of janitorial cleaning products is to combine and mix the chemical ingredients in a large tank. Manufacturers utilize one or more such large tanks, each tank typically being on the order of 500 gallons or more in volume and requiring a great deal of space. The tanks also require a suitable mechanism for mixing the cleaning chemicals. Once the finished product has been prepared, a suitable filler mechanism must be provided to dispense the mixed cleaning product into containers of suitable size for shipment.

There are several disadvantages inherent in the conventional production method. The process is very labor-intensive, requiring several operators to add the chemicals, control the mixing, fill the containers, etc. The large tanks also require substantial space, which increases the overhead cost of the manufacturing facility.

Another drawback of the conventional production method is that the quality of the final cleaning product may be inconsistent. It is often difficult to get the appropriate exact dilutions required for various applications, such as cleaning. Solutions which are too concentrated or too dilute may be unsuitable. There is substantial potential for operator error, for example, if an improper amount of component chemicals are added or if inadequate mixing occurs. Such errors can result in a poor quality product and can be costly due to waste of the raw materials. If the final cleaning product is chemically analyzed to monitor its quality, a substantial amount of analysis time is required, and skilled personnel must perform this analysis.

The present invention addresses the problems associated with conventional production methods.

SUMMARY OF THE INVENTION

The present invention comprises an apparatus for mixing and dispensing chemical solutions. The apparatus includes a manifold having a plurality of chemical inlet ports, a water inlet port, and an outlet port connected to a dispensing outlet for dispensing the chemical solutions and water into a container. A pump and valve means are associated with each of the chemical inlet ports to deliver the concentrated chemicals from a storage tank to the manifold. The apparatus also features several different embodiments of quality control means. The quality control means includes conductivity measurement means, weight measurement means, and volume flow measurement means. The apparatus also includes electronic control means associated with the pumps and valves to operate them in response to a preselected volume, sequential combination and concentration of chemicals so as to automatically produce the finished product with the desired components and concentration.

According to another aspect of the invention, a method of mixing and dispensing chemical solutions is disclosed. The steps of the inventive method include: positioning the dispensing outlet within the product container; pumping a plurality of concentrate chemicals through the valve means, manifold and dispensing outlet; metering a predetermined amount of water simultaneously with the concentrated chemicals through the manifold; automatically controlling the volume, sequence and concentration of the concentrated chemical flow; and monitoring the quality of the finished product.

A particular advantage of the present invention is that the cleaning solution is prepared and dispensed in the individual shipping container itself, rather than in a large tank. The dispensing system is suitable for use by a wide variety of companies, including manufacturers of chemical specialty products, distributers, and end users. Waste of the raw chemicals is minimized, because the exact required quantity of cleaning solution is produced according to the demands of the particular situation. This enables substantial cost savings for the user by greatly reducing the amount of floor space required to store large quantities of the raw materials and finished products. The entire lending and dispensing system, including chemical storage tanks, requires less than approximately 400 square feet of space. Labor costs are also reduced, because the apparatus of the present invention can be operated by a single worker who need not have specialized training.

The dispensing system of the present invention also produces the cleaning solutions in a relatively short period of time, allowing inventory needs to be met immediately. For example, a five gallon container of a cleaning solution with multiple ingredients can be mixed and dispensed in less than one minute. Changeover from the production of one type of cleaning product to another is also a simple matter, which provides substantial flexibility and convenience for the manufacturer. Rather than emptying and cleaning the large tank, or providing a plurality of tanks for different solutions, the apparatus of the present invention allows relatively small quantities of a particular solution to be produced, and then automatically cleans the supply lines before production of the next, different product.

Because the particular production demands can be met quite quickly, shelf life of the cleaning solutions can be shortened. As a result, the manufacturer need not add excess ingredients which may otherwise be necessary to extend the shelf life of the cleaning solution, such as thickeners or raw materials that tend to degrade over time.

The dispensing apparatus also includes means for preventing overfilling of the containers and spilling of the chemical solution outside the container. A unique drip cup design directs excess liquid into a drain, rather than allowing it to spill onto the outside of the container.

Another advantage of the present invention is an overall improvement in the quality and consistency of the finished product. The present invention is capable of mixing chemicals in an exact fashion and providing exact amounts of each ingredient desired, in combination with the appropriate dilution of water. The present invention also controls the quality of the final product by monitoring its conductivity, weight and/or volume. In the preferred embodiment, the container is weighed to assure that each of the chemical components has been dispensed in the proper amount. The preferred embodiment also monitors the conductivity of the cleaning solution as it is being prepared, which provides an additional basis for correcting possible errors. The operator is notified of the possible error immediately, and the product can be corrected quickly without producing a large quantity of poor-quality cleaning solution.

Another feature of the present invention is the automatic recordation of the type of cleaning solutions produced and the number of containers filled. This facilitates inventory control and is useful for billing purposes.

Safety of operation is another advantage of the present invention. The operator need not handle the raw chemicals, some of which may be dangerous. There is no problem with spillage and drippage of the chemicals outside the shipping container. Further, the chemical ingredients are added in a suitable sequential order to prevent chemical combinations which may be unstable.

The dispensing system of the present invention, while disclosing an embodiment tailored for cleaning chemicals, is also suited for any number of other uses.

These and other features of the invention will become apparent from a consideration of the following description of the invention and accompanying drawings which form a part of this application.

BRIEF DESCRIPTION OF THE DRAWINGS

The present invention will be more particularly described with respect to the accompanying drawings, wherein.

DESCRIPTION OF THE PREFERRED EMBODIMENT

Figure 1:
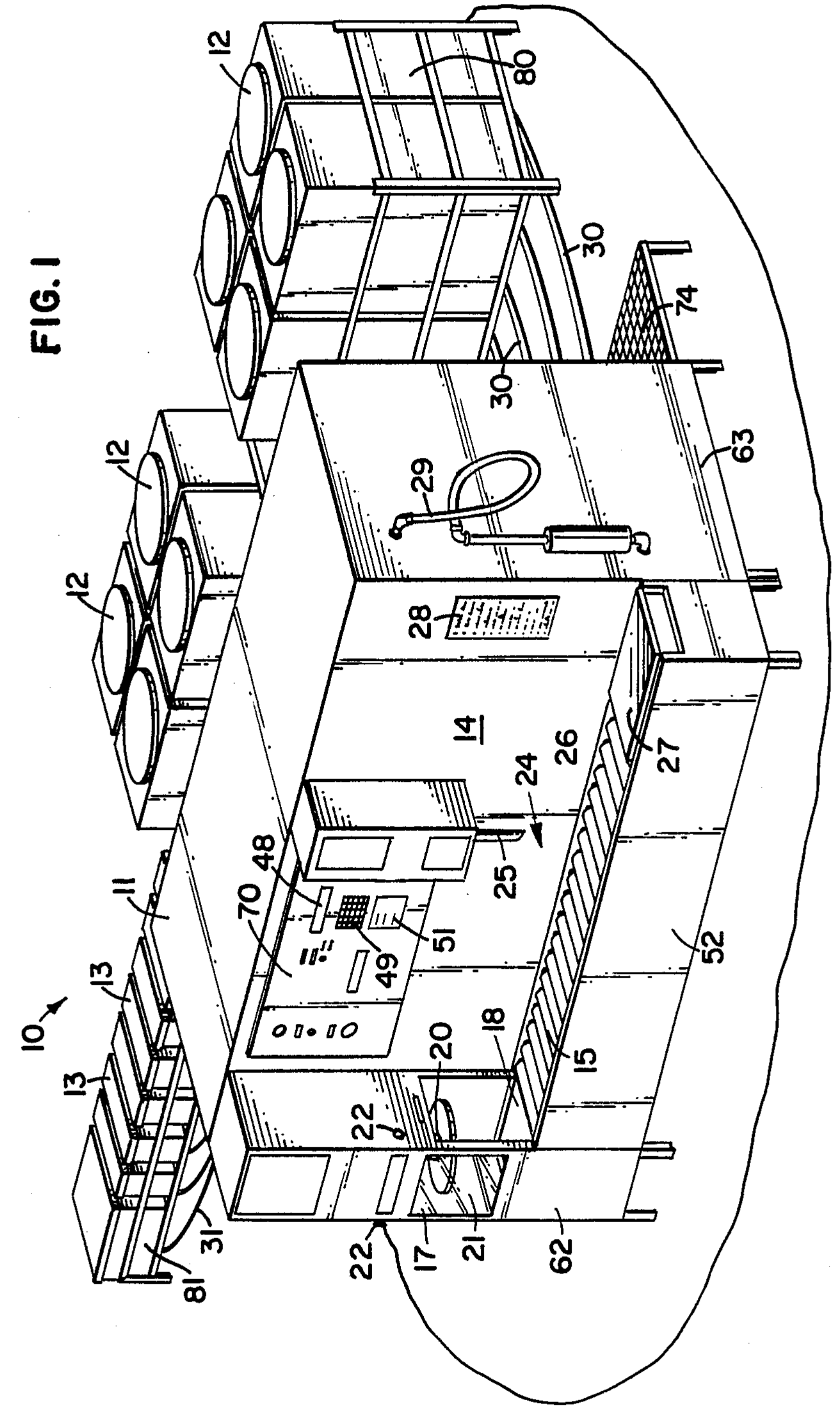
FIG. 1 is a perspective view of the chemical mixing and dispensing system of the present invention.

The chemical mixing and dispensing apparatus 10 of the present invention is shown generally in FIG. 1. The dispensing apparatus 10 includes a free-standing blending unit 11; a plurality of storage tanks 12 for containing the concentrated bases 80; and a plurality of storage tanks 13 for containing dyes and/or perfumes 81. The blending unit 11 has a front wall 14 and side walls 62, 63. A walkway 74 may also be provided proximate the rear of the blending unit cabinet 11 to facilitate inspection and maintenance of the apparatus 10. Along the front wall 14 of the cabinet 11 is a conveyor belt 15 or other suitable support means upon which is placed the container 16 into which the finished product will be dispensed. The containers 16 can be a variety of sizes, ranging in volume from five gallons to fifty-five gallons in the preferred embodiment.

Beneath the conveyor belt 15 is a tank 52 suitable for the collection of excess water and chemicals. The bottom of the tank slopes slightly to one end, with a drain (not shown) being provided at the lower end of the tank 52.

Figure 3:
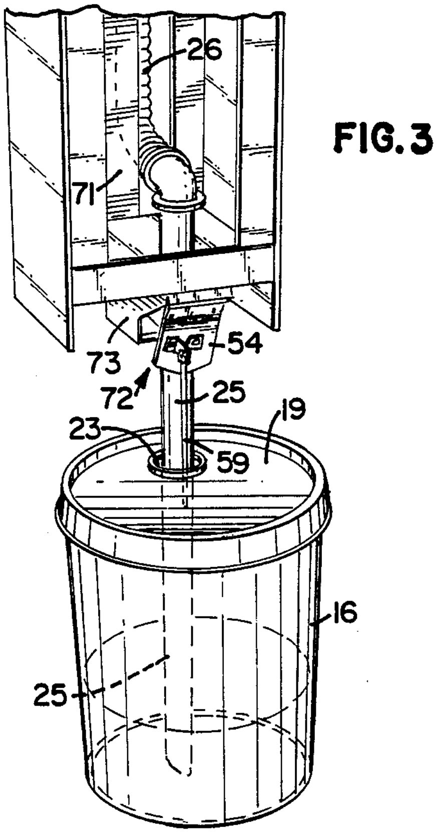
FIG. 3 is a perspective view of the dispensing tube and drip collector in the down position.

On the left side (as viewed in FIG. 1) of the cabinet 11 is a lid attachment station 17. The lid attachment station 17 contains a platform 18 upon which the product container 16 is supported. In the preferred embodiment, the container lid 19 is securedly attached to the top of the container 16 by means of a downwardly moving pneumatic ram 20. A gasket (not shown) on the lid 19 snaps into place within a corresponding rim (not shown) in the container 16 to securedly attach the lid 19 in place. Preferably, the lid attachment station 17 is surrounded by safety walls 21 which protect the operator from injury. Operation of the ram 20 is controlled by control buttons 22. Preferably, both the control buttons 22 must be pressed simultaneously to activate the pneumatic ram 20. The lid 19 completely covers the top of the container 16 except for a relatively small dispensing hole 23 through which the ingredients will be dispensed, as illustrated in FIG. 3.

A labeling station (not shown) may also be provided proximate the apparatus 10 in order to secure an appropriate label to the product container 16 before the lid 19 is attached.

The blending unit 11 has a dispensing station 24, where the container 16 is positioned during the dispensing cycle. The ingredients enter the container 16 via a dispensing tube 25 which is preferably formed of opaque plastic tubing. The dispensing tube or fill head 25 is sized and configured so as to fit within the hole 23 of the lid 19. The container 16 is positioned upon the conveyor belt 15 beneath the dispensing tube 25 so as to align the fill head 25 with the hole 23. There is a hanging marker pin 59 which extends from a plate 54 to facilitate centering of the pail 16 beneath the dispensing tube 25 by the operator. The dispensing tube or fill head 25 moves between an up, non-operative position and a down, dispensing position as shown in FIG. 3. In the down position, the dispensing tube 25 extends into the container 16 so as to be approximately one-half inch from the bottom of the container 16, as illustrated in FIG. 3. In the up position, the fill head 25 is contained within the dispensing tube frame 73.

In the preferred embodiment, the vertical movement of the dispensing tube 25 is controlled by pneumatic means, including a vertically movable pneumatic cylinder 71. If the dispensing hole 23 is not in proper alignment and the downwardly moving dispensing tube 25 hits the top of the lid 19, the dispensing tube 25 will return to its upward position so that the operator can readjust the position of the container 16. The pneumatic cylinder 71 which controls the vertical movement of the dispensing tube 25 has two proximity switches (not shown), an upper switch and a lower switch. When the fill head 25 begins its descent, it activates the upper switch, and when the fill head reaches its down position, the second, lower switch is activated. However, in the event that the fill head 25 abuts against the lid 19 and is prevented from continued downward movement, the lower proximity switch is not activated. The electronic control unit 70 of the present invention then automatically returns the dispensing tube 25 to its upper, non-dispensing position in the event that the second, lower switch is not activated within a predetermined time (three seconds in the preferred embodiment) after activation of the first, upper switch.

Figure 2:
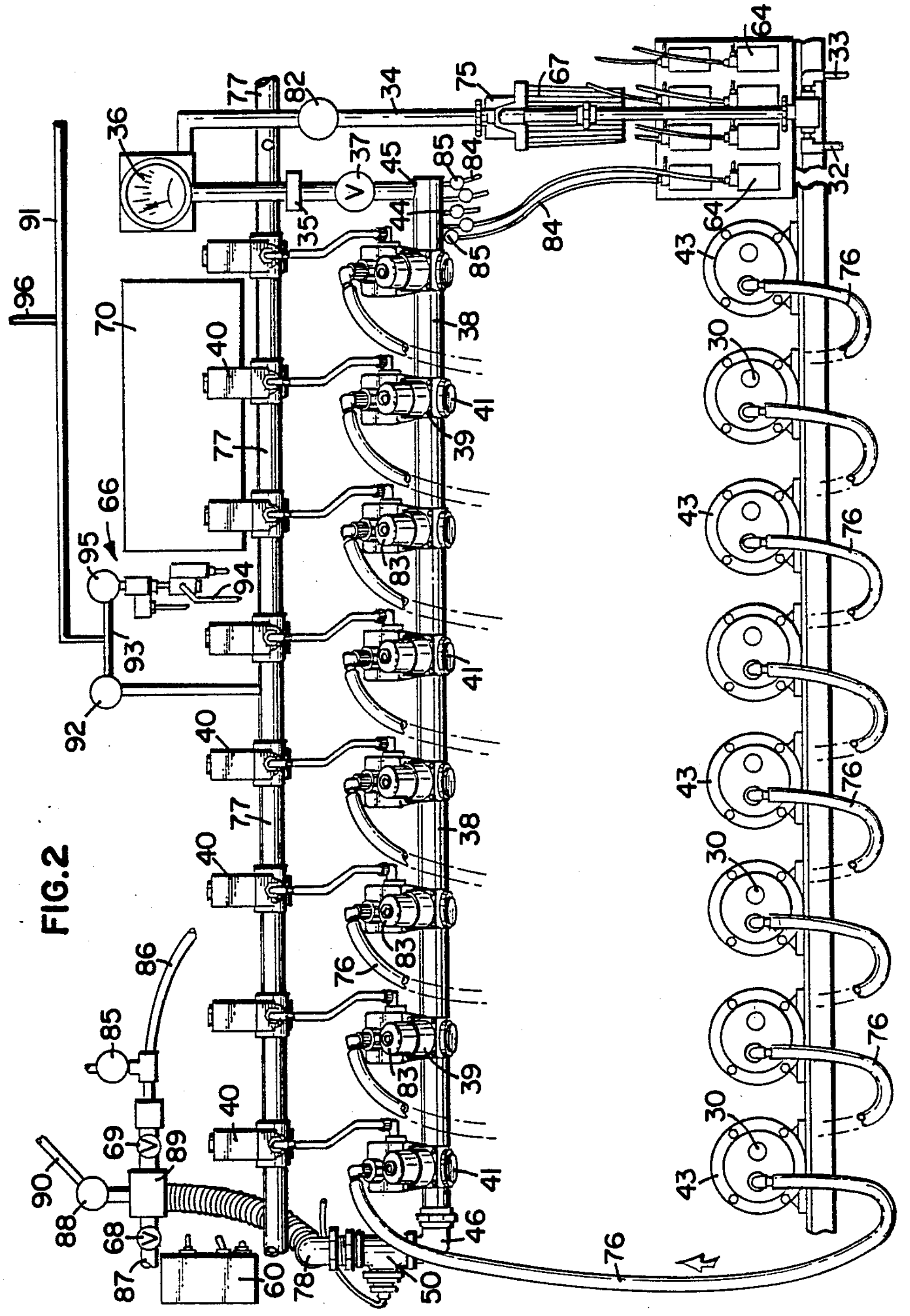
FIG. 2 is a rear elevational view of the dispensing apparatus.

Suitable pneumatic hoses and control valves are provided to control movement of the lid attachment ram 20 and movement of the dispensing tube 25, as illustrated in FIG. 2 and discussed below. After the container 16 has been filled, the control means 70 activates the pneumatic valve so as to withdraw the fill head 25 from the container 16 at two different speeds As the fill head 25 rises through most of the container 16 filled with liquid, it moves at a first, lower speed and then it increases in velocity when the fill head 25 breaks the surface of the liquid. This dual speed withdrawal of the fill head 25 allows for the maximum fluid to be drained within the container 16, so as to minimize or eliminate undesirable spillage outside the container 16. In the preferred embodiment, the dual speed withdrawal of the fill head 25 is controlled by the use of two solenoids (not shown) which control the supply of air to the pneumatic cylinder 71. The first solenoid has a muffler mechanism so as to allow only a limited amount of air therethrough and so as to cause the withdrawal speed to be relatively slow. The second solenoid has no such muffler mechanism, thereby allowing a relatively greater amount of air to pass therethrough and increasing the speed of withdrawal. The control means 70 activates the two solenoids in the proper manner based upon a predetermined amount of time as determined by the container size.

An air inlet line 91 transports air from a suitable air supply (not shown) for the dispensing station 24, lid attachment station 17 and concentrate valves 41. The inlet line 91 is maintained at an appropriate pressure by pressure regulator 92. Pneumatic means 66 controls movement of the fill head 25 and has an inlet line 93 and outlet line 94 interconnected to the pneumatic cylinder 71. The proper pressure is maintained in inlet line 93 by pressure regulator 95. The pneumatic control means 66 for the dispensing outlet 25 is similar in construction to pneumatic control means (not shown) for the lid attachment mechanism located at point 96 on the air inlet line 91.

In the preferred embodiment, a secondary dispensing tube 29 is provided at the right end of the cabinet 11 on the side wall 63. The tube 29 is utilized for filling relatively large drums 16, such as a fifty-five gallon container (not shown). The dispensing tube 29 is manually placed within the product drum 16, rather than being automatically moved into place as described above with dispensing tube 25.

On the right end of the dispenser 10, as viewed in FIG. 1, is a weighing station 26. The weighing station 26 includes a scale 27 and weight display 28. The weighing station 26 is utilized for purposes of quality control, as described below.

Figure 4:
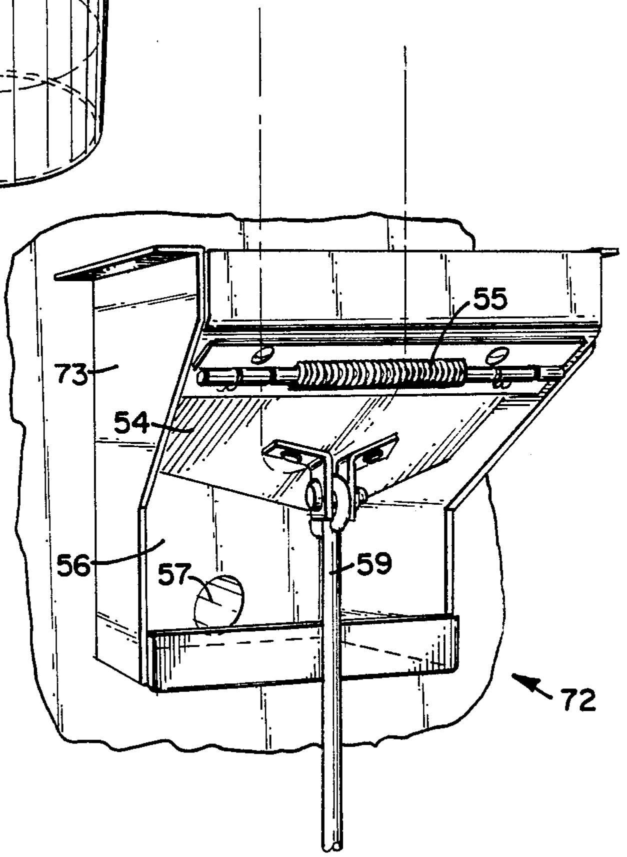
FIG. 4 is a perspective view of the drip collector illustrated in FIG. 3, in the up position.

Another novel feature of the present invention is the drip cup assembly 72, illustrated in FIGS. 3 and 4. The drip cup assembly 72 is positioned at the dispensing station 24, and is mounted to a frame 73 by means of a spring-loaded hinge 55. The drip cup assembly 72 has a drainage cavity 56 into which excess fluid is directed. A movable plate 64 rotates about the hinge 55 and directs the excess fluid into the drainage cavity 56. The drainage cavity 56 has a sloped bottom and a drain 57 at one end thereof. When the dispensing tube 25 is lowered, the tongue or plate 54 is pushed by the dispensing tube 25 so as to rotate downwardly as shown in FIG. 3. After the dispensing cycle is complete and the dispensing tube 24 is raised, the tongue 54 collects any remaining drops of solution and directs them into the drainage cavity 56. The drain 57 within the cavity 56 is interconnected by suitable tubing to the drain within the tank 52. In this manner, any excess chemical solution is not dripped onto the outside of the shipping container 16, which could otherwise present a safety hazard for persons handling the container 16.

In the preferred embodiment illustrated, there are eight chemical storage tanks 12 containing the concentrates 80, as illustrated in FIG. 1. Intake tubes 30 extend into the tanks 12 of concentrate 80 and are connected inside the dispenser 10 as described below. Any number of concentrates 80 may be utilized with the present invention. A second set of tanks 13 contains a plurality of dye and perfume solutions 81. The dye and perfume solutions 81 are interconnected to suitable intake tubes 31 for transporting of the dyes and perfumes into the dispenser 10 as described below.

Each ingredient tank 12, 13 is provided with suitable electrical sensing means (not shown) for monitoring the amount of ingredient in each tank 12, 13. The electrical sensors indicate to the control unit 70 when a particular chemical supply is too low to allow the product selected to be mixed and dispensed. In that event, the computer notifies the operator which of the tanks 12, 13 needs to be replenished. The electrical probes are set at a different level in each supply tank 12, 13 according to the amount of the ingredient which needs to be withdrawn as required by the product formulation needs. In the preferred embodiment, the sensing means for the dye and perfume tanks 13 consists of a float which makes electrical contact when the fluid level has dropped to a sufficiently low point. The concentrate tanks 12 preferably have an electrical sensing means which includes three electrodes: a reference electrode, an electrode positioned near the bottom of the tank 12, and electrode positioned near the upper portion of the tank 12. When the fluid level descends below the reference electrode, the electrical circuit is broken, and an appropriate indication is made to the control means 70. The upper electrode prevents overfilling of the storage tanks 12.

Referring to FIG. 2, the blending unit 11 has water lines 32 and 33 connected to sources of hot and cold water, respectively. A water inlet tube 34 is provided with a water pressure regulator 82 having a flow control mechanism so as to provide a constant flow of volume and prevent excess water inlet pressure. The water inlet line 34 is also provided with a vacuum breaker 75 in order to prevent the backflow of chemicals into the water supply in the event of a drop in water pressure A flow meter 36 measures the water flow and assures that the product container 16 reaches the correct fill level. A water filter 67 acts to rid the water of rust and other undesirable impurities. A selectively controllable water solenoid valve 35 is also provided along the water inlet tube 34 in order to regulate the incoming flow of water. Preferably, a water inlet check valve 37 is attached to the solenoid outlet, which provides additional protection against the backflow of chemicals.

Figure 6:
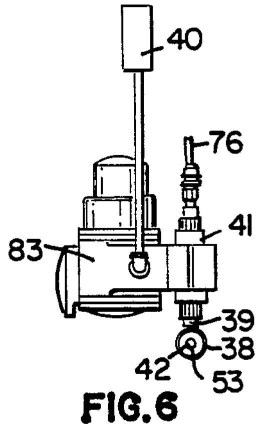
FIG. 6 is a sectional view of the manifold, chemical inlet port and valve of the present invention.

The dispenser 10 includes a longitudinal manifold 38 having a central passage 42 therein, as illustrated in FIGS. 2 and 6. A plurality of chemical inlet passages 39 are in fluid communication with the manifold's central passage 42. The manifold 38 is supported within the cabinet by suitable support means or frame members (not shown). The chemical inlet ports 39 are interconnected to the manifold 38 by suitable means such as welding or by threaded connection. A flush port or water inlet port 45 is located at one end of the manifold 38 for purposes of inletting water from the water inlet line 34. At the opposite end of the manifold 38 from the flush port 45 is a manifold outlet 46.

In the preferred embodiment, the manifold 38 has a static mixer 53 within its central passage 42. The static mixer 53 preferably extends throughout the length of the manifold 38 and is shaped like an auger so as to provide turbulence and mixing of the chemical ingredients as they flow through the manifold 38. Alternatively, the static mixer could be positioned in only a portion of the manifold proximate the outlet end 46. In addition, static mixer 53 prevents any of the concentrates 80 from forming a gel in the manifold 38 after coming into contact with the water.

Each of the chemical inlet ports 39 has a selectively controllable valve means 41. Each valve 41 is connected to a concentrate inlet line 76, the inlet lines 76 being cut away for purposes of clarity in the view illustrated in FIG. 2. FIG. 6 illustrates a sectional view of the valve 41, the inlet port 39, and manifold 38. In the preferred embodiment, the valves 41 are pneumatically actuated ball valves. The ball valves 41 are of the type manufactured by GF Company. The air intake into the ball valves is controlled by corresponding solenoids 40 which are interconnected to an air manifold 77.

The valve actuators 83 are spring-loaded with the actuator plunger (not shown) normally being in a position so as to cause the ball valve 41 to occlude fluid flow. Upon energization of the solenoid 40, the actuator plunger retracts, thereby allowing the corresponding valve 41 to open and fluid to flow through the chemical inlet port 39 and into the central manifold passage 42. Movement of the actuator spring and plunger causes rotation of a pinion gear in the actuator 83, the pinion gear being interconnected to the ball valve 41 so as to cause the valve 41 to open or close. The valves 41 have a relatively short response time on the order of tens of milliseconds.

Each of the intake tubes 30 from the storage tanks 12 has a pump 43 for delivering the concentrate 80 into the manifold 38. In the preferred embodiment, the pumps 43 are located proximate the bottom of the cabinet 11. Preferably, the pumps 43 utilized are positive displacement pumps, either magnetic drive gear pumps or direct drive gear pumps. The magnetic drive pumps provide little or no leakage, and a suitable pump for this type of application is the magnetic drive gear pump manufactured by the Tuthill Pump Company of California. The speed of the pumps is calibrated by pump drive control mechanisms 60 located along the side wall 63 of the cabinet 11. Generally, the pumps run on the order of 3,000–8,000 milliliters/minute, and the concentrates 80 are delivered at approximately one to two gallons per minute. Preferably, the pumps 43 are powered by AC motors. The volume delivered by the pumps 43 is measured either in terms of pumping time, as described in detail below in the Examples, or by the number of revolutions of the pump motor. The predetermined pump run time takes into account the lowered pumping output as the pump 43 starts and reaches its normal operating speed.

The control unit 70 causes the ball valve 41 to open at the same time that the corresponding pump 43 is activated. This prevents a build-up of back pressure in the inlet line 76 which could automatically deactivate the pump 43.

Because the various chemical concentrates 80 have different viscosities and other flow characteristics, the control mechanism 70 accounts for these varying rates in controlling the amount of fluid 80 pumped. In addition, the diameter of inlet line 76 and the type of material utilized is dependent upon the particular chemical concentrate 80 being pumped. The majority of the inlet lines 30, 76 can be made of a plastic material such as PVC, although a few of the concentrates may adversely affect this type of material and therefore require an inlet line 30, 76 made of a material such as Teflon-coated stainless steel.

Also provided are pumps 64 for the injection of the dyes and perfumes 13 into the manifold 38. In the preferred embodiment, the pumps 64 for delivery of the dye and perfume solutions 81 may be bellows pumps, peristaltic pumps, or piston pumps. These types of pumps are useful because of their ability to pump relatively small volumes in accurate quantities. There are a plurality of inlet ports 44 in the manifold 38 interconnected to the dye and perfume inlet lines 84. The inlet lines 84 are provided with suitable control valves 85, which are check valves in the preferred embodiment.

Preferably, the most dangerous concentrates 13 are positioned on the left end of the manifold 38, as viewed in FIG. 2, in order to reduce the likelihood of undesirable chemical reactions with the other chemicals flowing through the manifold 38. In addition, the concentrates are pumped sequentially in such a manner so that potentially unstable combinations of the concentrates are pumped through the manifold 38 at different times. For example, Concentrates C and F are staggered from each other, as are Concentrates B and E, because these combinations could result in precipitation in the manifold 38.

A circuit board in the control unit 70 contains the microprocessor electronics which provide the control functions for the dispenser 10. An LED board 48 is mounted to the front wall 14 and displays information to the operator in response to punching of various buttons on the membrane switch 49. A power supply (not shown) supplies proper levels of power for the various components described above.

In the preferred embodiment, the microprocessor of the present invention also includes memory means which automatically inventories the type of product dispensed, the size container, and the number of containers 16. This allows the operator to accurately monitor and control inventory. The apparatus 10 can be provided with a modem (not shown) to transmit inventory and conductivity information to a remote location. This feature may be useful for trouble-shooting purposes, billing purposes, etc.

In the preferred embodiment, a laser bar code reader (not shown) is positioned proximate the dispensing station 24. The bar code reader reads a bar code (not shown) on the label of the container 16 as the container is being filled. The control unit 70 then records the information from the bar code into its memory for inventory purposes. The bar code reader also serves as a useful verification that the operator has inputted the correct product information, thereby assuring that the label on the product container is consistent with the type of product contained therein.

Proximate the outlet port 46 of the manifold 38 is a conductivity cell 50. The conductivity cell 50 measures the electric conductivity of the chemical solution which is being passed through the outlet end 46 of the manifold 38. In the preferred embodiment, an electrodeless conductivity cell is utilized, e.g., of the type manufactured by The Foxburo Company of Mass. and described in U.S. Pat. No. 4,733,798. In the preferred embodiment, the conductivity cell 50 is interconnected to the control unit 70 so as to record conductivity against time. The graphical output of conductivity versus time for the various products being dispensed provides a useful basis for trouble-shooting and monitoring of the quality of the final product, as described below in the Examples. That is, the conductivity output is capable of indicating the absence of a concentrate 80, which would occur in the event that a pump 43 or valve 41 malfunctions.

In the preferred embodiment, the manifold 32 is sloped to be slightly higher on its left side (as viewed in FIG. 2). Preferably, the conductivity cell is also positioned to be mounted upon a vertical portion 78 of the fluid line.

Positioned downstream from the conductivity cell 50 is a tee intersection 89, the right side of the tee having an outlet line 86 and leading to the dispensing tube 24 (which is utilized for the filling of relatively small containers 16), and the left side of the tee having an outlet line 87 and leading to the secondary dispensing tube 29 (for the filling of large drums). The flow of solution is controlled around the vicinity of the tee intersection by suitable blocking valves 68, 69 on each side of the tee, which are automatically activated by the control unit 70 of the present invention.

In operation, the operator presses the "on" switch on membrane switch 49 and selects the size of container 16 which will be utilized. The operator then inputs the code for the product desired. In the preferred embodiment, the list of products mixed and dispensed by the apparatus 10 and their corresponding codes are listed on a menu 51 attached to the front wall 14 of the cabinet 11. The operator then attaches the lid onto the container 16 at the lid attachment station 17.

The container 16 is moved to the dispensing station 24, whereupon the "start" button is pressed. Upon the "start" button being pressed, the dispensing tube 25 lowers into the container 16. The water solenoid valve 35 then opens and runs the entire time during the dispensing operation. In the preferred embodiment, the water is delivered at approximately four gallons per minute. The water provides both a necessary ingredient for the finished product and means by which the manifold 38 is continuously flushed. In addition to providing the necessary dilution, the water also facilitates the conductivity measurement of the relatively high-conductivity concentrates 80.

In the preferred embodiment, an initial flush of water for approximately two seconds is sent through the manifold 38 but is not dispensed into the container 16. This allows flushing of the manifold 38 to occur and also allows for the fluid line 78 proximate the conductivity cell 50 to be filled in order to eliminate any air bubbles around the conductivity cell 50 which could adversely affect the accuracy of the conductivity measurements. When the initial flush occurs, both blocking valves 68, 69 are closed. During the initial flush, a purge solenoid 88 is activated which is proximate the tee intersection 89. Activation of the purge solenoid 88 causes the water to drain through a drainage line 90 which runs to the tank 52.

The control unit 70 then causes the purge solenoid 88 to close and the appropriate blocking valve 68, 69 to open, whereupon an initial amount of water is dispensed into the bottom of the pail 16 to a level at which the end of the dispensing tube 25 is submerged in order to prevent foaming. Preferably, for a five gallon container, the initial water delivery occurs for approximately six seconds, and the first concentrate is added six seconds into the dispensing cycle. As the dispensing cycle progresses and the product is manufactured, water continues to run through the manifold 38 and be dispensed into the container 16 at a rate of approximately four gallons per minute in the preferred embodiment. Shortly after the water cycle begins, the concentrate pumps 43 and valves 41 begin sequencing on and off according to the product program. Preferably, the program allows the operator to choose any volume of product to be dispensed in five gallon increments ranging between five gallons and 55 gallons.

At the predetermined time, the concentrates 80 are delivered; i.e., the appropriate pump 43 is automatically activated and the corresponding valve 41 is opened so as to pump the first ingredient or base concentrate 12 into the manifold 38, through the outlet port 46 and through the dispensing tube 25. The pump 43 and solenoid 40 are activated at the same time. When the allotted amount of the first chemical has been dispensed, the solenoid 40 closes and the pump 43 deactivates.

Preferably, multiple concentrates 80 are dispensed simultaneously, thereby greatly reducing the total amount of time needed to fill the product container 16. However, the addition of the concentrates 80 is staggered by the control means 70 in order to be able to properly evaluate conductivity. The multiple ingredients 80 are pumped simultaneously with the continuous flow of water through the manifold 38. The appropriate amount of dye and/or perfume 81 is also added at the appropriate time by activation of the corresponding pump 64. After the final ingredient has been dispensed, there is a final flush of water which cleans out any traces of the prior chemicals. Preferably, the final flush consists of approximately one-half gallon of water, and lasts for approximately six seconds for a five gallon container.

It should be noted that the dispensing of the concentrates into the container 16 by means of the tubes 25, 29 provides sufficient turbulence and mixing within the product container 16 so as to alleviate the need for an additional mixing mechanism. Thus, the product constituents are mixed as they are being dispensed.

After the flush cycle is completed, the water solenoid 35 shuts off, typically leaving some amount of liquid remaining in the manifold 38. The control unit 70 then causes the activation of a vent solenoid 85. The vent solenoid 85 is located on one or both of the product dispensing lines 86, 87 which lead to the dispensing nozzles 26, 29, respectively. When the vent solenoid 85 is activated, the fluid line 86 is vented to the atmosphere thereby removing the vacuum within the line and causing the remaining fluid therein to be drained into the container 16.

While the various chemicals are pumped through the manifold 38 and into the product container 16, the conductivity cell 50 monitors the conductivity continuously. This conductivity measurement assures that the proper concentrates 80 are being dispensed. In the preferred embodiment, the actual conductivity versus time output for a particular dispensing cycle is compared to a "control" conductivity output, either manually or automatically, thereby allowing the operator to detect possible malfunctions in the system 10.

At the weighing station 26, a scale is provided to determine the weight of the full container 16. This actual weight is compared either manually or automatically by the control unit 70 to the specified weight range for that particular product formulation. The weight range for the different types of product is determined according to the specific gravity of the ingredients. For example, a weight range of ±0.5 pounds for a five gallon container provides a ±1% permissible weight variation and is suitable for verifying that the product container is not missing a major constituent. In the preferred embodiment, a weight display board 28 notifies the operator whether the weight of the full container 16 is within the weight range or outside the weight range.

An alternative quality control means to the aforementioned weight method is to provide a flow meter (not shown) proximate the conductivity cell 50. The flow meter measures the total volume running through the manifold outlet and into the container 16 during a dispensing cycle, thereby notifying the operator in the event of a pump malfunction which would result in a particular concentrate 80 not being delivered.

In the event that the above-described weight or volume monitoring means indicates a pump malfunction, the conductivity measurements are then compared to determine the likely source of the problem. This comparison of conductivity measurements can be done either manually or by suitable automatic control means.

After the dispensing cycle is completed, the operator places a cap (not shown) over the dispensing hole 23 before stocking the product. The finished product is then ready to be shipped in the shipping container 16.

Table I shows preferred exemplary weight percentages for the various ingredients which are utilized in forming various exemplary chemical cleaning products. The concentrates A–H referred to in Table I are as follows: Concentrate A, surfactant (anionic); Concentrate B, solvent blend; Concentrate C, caustic; Concentrate D, water conditioner; Concentrate G, surfactant (anionic), and Concentrate H, surfactant (anionic). The particular chemical formulations for these types of concentrates depends upon the particular application involved and the chemical characteristics desired.

TABLE 1

| | PRODUCT FORMULATIONS (Percent by Weight) | | | | | | | | | | | | | |
|---|---|---|---|---|---|---|---|---|---|---|---|---|---|---|
| | CONCENTRATES (%) | | | | | | | | DYES/PERFUMES (%) | | | | | |
| PRODUCT | A | B | C | D | E | F | G | H | BLUE | YELLOW | LEMON | APPLE | PINE | WATER (%) |
| Floor Stripper | | 10.0 | 2.0 | 3.5 | 3.6 | 6.0 | 2.5 | | 0.14 | 0.14 | | | 0.10 | 69.98 |
| All Purpose Cleaner | 10.0 | | | 6.0 | | 0.1 | | | | 0.15 | | | | 83.75 |
| Bathroom Cleaner | 5.0 | 5.0 | | | | 7.0 | | | | | 0.30 | 0.14 | | 82.56 |
| Heavy Duty Degreaser | 5.0 | 16.0 | 4.8 | | | 0.4 | | | | | | | | 73.80 |
| Carpet Extract | | | | 1.0 | | 10.0 | 10.0 | | | 0.10 | | 0.10 | | 78.80 |
| Carpet Shampoo | | | | | | 0.1 | 0.96 | 40.0 | | | 0.20 | | | 58.74 |
| Carpet Spot Prespray | | 20.0 | | | | 1.5 | 10.0 | | | 0.10 | | 0.10 | | 68.30 |
| Floor Cleaner | | 10.0 | 1.5 | 4.0 | 1.5 | 4.5 | 1.0 | | | | | | | 77.50 |
| General Purpose Detergent | 20.0 | | | | | 0.1 | | | | 0.13 | | | | 79.77 |
| Vehicle Wash Detergent | 5.0 | | 1.8 | 3.5 | 1.0 | 5.0 | 1.8 | | | | 0.40 | | | 81.52 |

Figure 5:
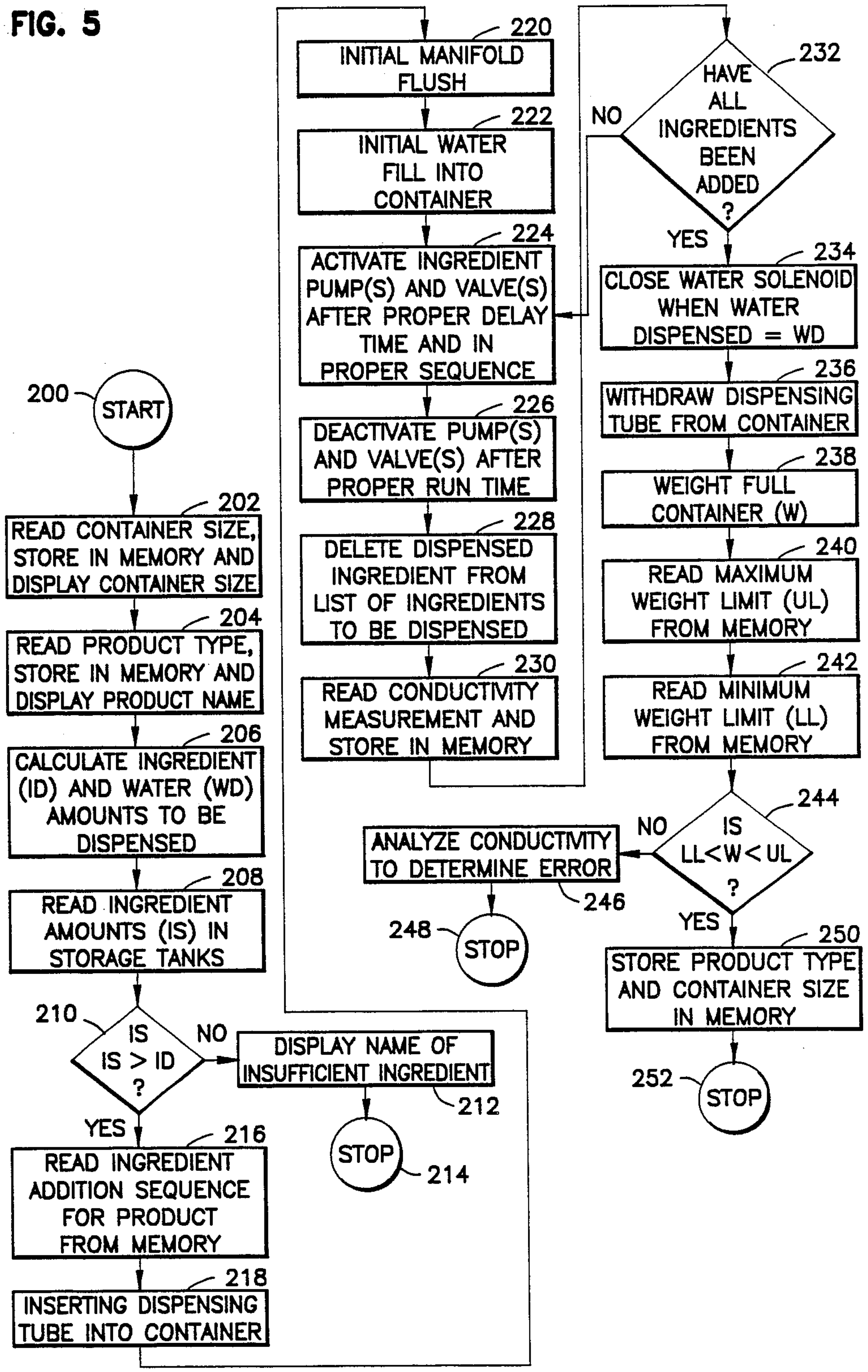
FIG. 5 is a flow chart of the preferred form of a microprocessor control for the present invention.

FIG. 5 illustrates a flow chart of the preferred form of implementation of the controller 70 for the invention which utilizes a microprocessor to control the system operation. At the starting point 200 of the microprocessor control program, it is assumed that the following sequence of events has occurred: product formulations, amounts, and sequencing has been entered; the amount of water to be dispensed for each product type and container size has been entered; the power has been turned on; the container 16 has been labeled; maximum and minimum weights UL and LL for the full containers of the various types of products have been entered; and the container 16 is in a position to receive the chemical solutions to be dispensed. The program proceeds to block 202 where the container size is stored in memory based upon the information entered by the operator, and the container size is displayed to verify this information to the operator. Similarly, block 204 reads the product type from the information code entered by the operator, stores the product type in memory and displays the name of the product for the operator's reference. The program then proceeds to block 206 where the product ingredient amounts (ID) and water amounts (WD) to be dispensed are calculated according to the size and type of product, based upon product information which is already in the controller's memory. The program then proceeds to block 208 where the controller determines the amount of chemical solution 13 in the storage tanks 12 (IS) by means of the electrical sensors. The program then proceeds to the decision point 210 where a determination is made if IS>ID. If the answer is "no", the program branches to block 212 where the name of the insufficient ingredient is displayed to indicate that a particular storage tank 12 needs to be filled in order to make that particular product. The program then proceeds to stopping point 214 which terminates all activity. If the answer is "yes" at decision point 210, the program proceeds to block 216 where the controller 70 reads the ingredient addition sequence, i.e., the order and amounts of the various concentrates and water, for the product entered This information is all stored in the controller's memory. The program then proceeds to block 218, where the appropriate dispensing tube 25 or 29 is inserted into the container 16.

The program then proceeds to block 220 where the controller 70 causes the water solenoid 35 and the purge solenoid 88 to open to initiate the two-second initial manifold flush. The purge solenoid 88 then closes, and at block 222, the dispensing cycle begins with the initial water fill of approximately six seconds (for a five gallon container) into the container 16. The program then proceeds to block 224 where the pumps 43 and valves 41 are activated in the proper sequence and after the proper delay time, according to the information stored in memory. As shown at block 226, the pumps and valves are deactivated by the controller 70 after the proper run time. The program then proceeds to block 228 where the dispensed ingredient or concentrate is deleted from the memory's list of ingredients to be dispensed. As shown at block 230, the controller 70 reads the conductivity measurements from the conductivity cell 50 during the dispensing cycle and stores these measurements in memory. The program then proceeds to decision point 232 where a determination is made as to whether all of the ingredients have been added, i.e., whether all of the concentrates, dyes and perfumes have been dispensed through the manifold 38 and into the container 16. If the answer is "no", the program loops back to block 224 where the activation of the appropriate pumps and valves occurs for the remaining ingredients. If the answer is "yes", the program proceeds to block 234 where the controller 70 closes the solenoid 35 on the water inlet line 34 when the water which has been dispensed equals WD, the predetermined amount of water to be dispensed for that particular product. The water dispensed is measured by the flow meter 36. The water solenoid is not closed until after all of the ingredients have been added, with the additional lag time (between dispensing of the final concentrate and the end of the dispensing cycle) providing a final water flush. The vent solenoid 85 is then activated to drain the fluid line. The program then proceeds to block 236 where the dispensing tube 25 or 29 is withdrawn from the container 16. The program then proceeds to block 238 where the full container 16 is weighed. At blocks 240 and 242, the controller 70 reads the maximum weight limit (UL) and the minimum weight limit (LL) from memory. The program then proceeds to decision point 244 where the determination is made as to whether the actual weight of the full container 16 is within the weight specification for that particular product. If the answer is "no", the program proceeds to block 246 where the conductivity measurement is analyzed, either manually or by the controller 70, and compared to the standard conductivity read-out for that particular product in order to determine the error in the dispensed product. The program then proceeds to stopping point 248 which terminates all activity in the program. If the answer is "yes" at decision point 244, then the controller 70 stores the inventory information in its memory, i.e., the product type and the container size. This inventory information is continually updated. The program then proceeds to stopping point 252 which terminates all activity in the program.

The following are particular examples which demonstrate the mixing and dispensing of two particular chemical solutions and the operation of the quality control means.

EXAMPLE I

Figure 7:
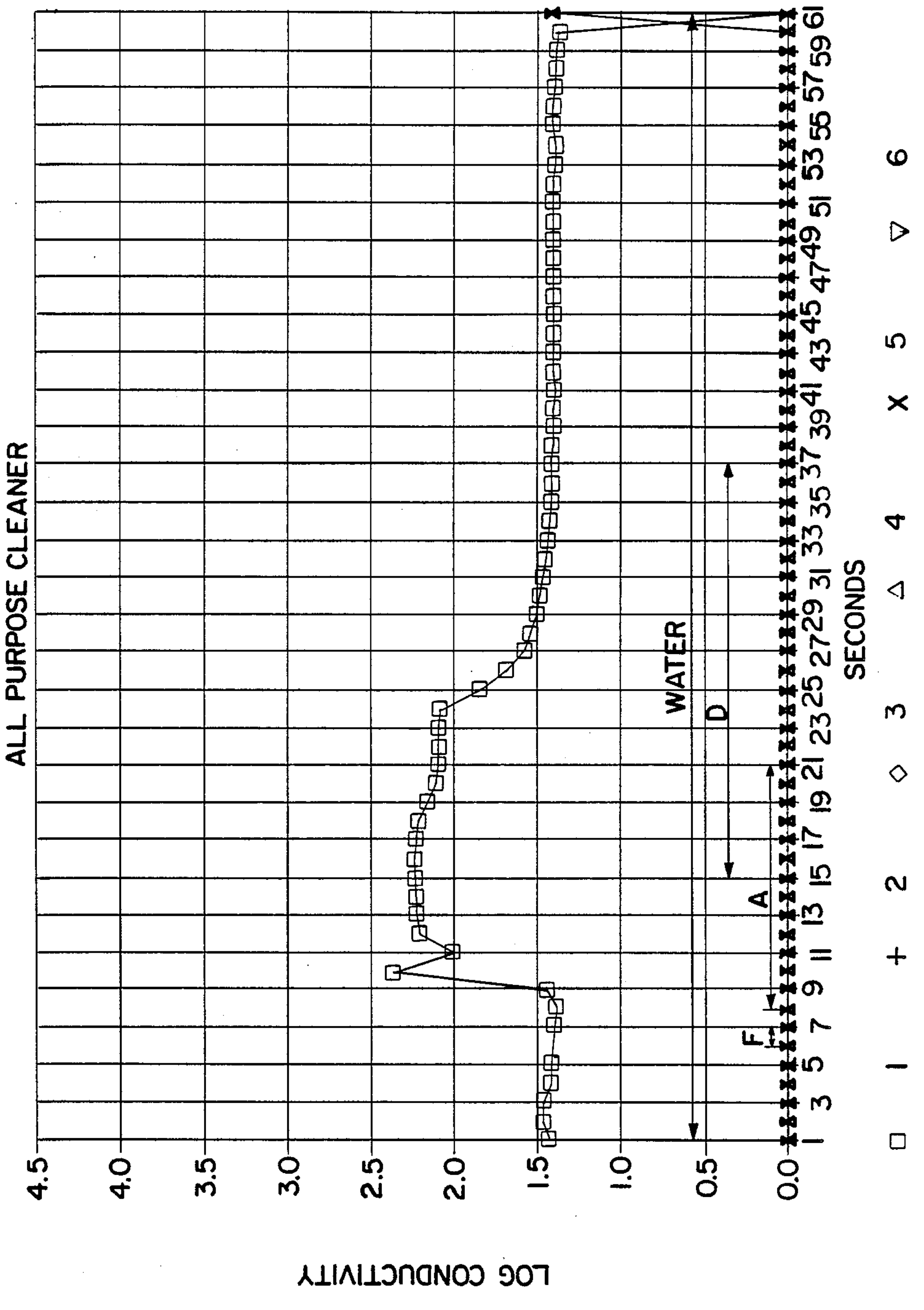
FIG. 7 is a conductivity graph for the product formulation described in Example I.
Figure 8:
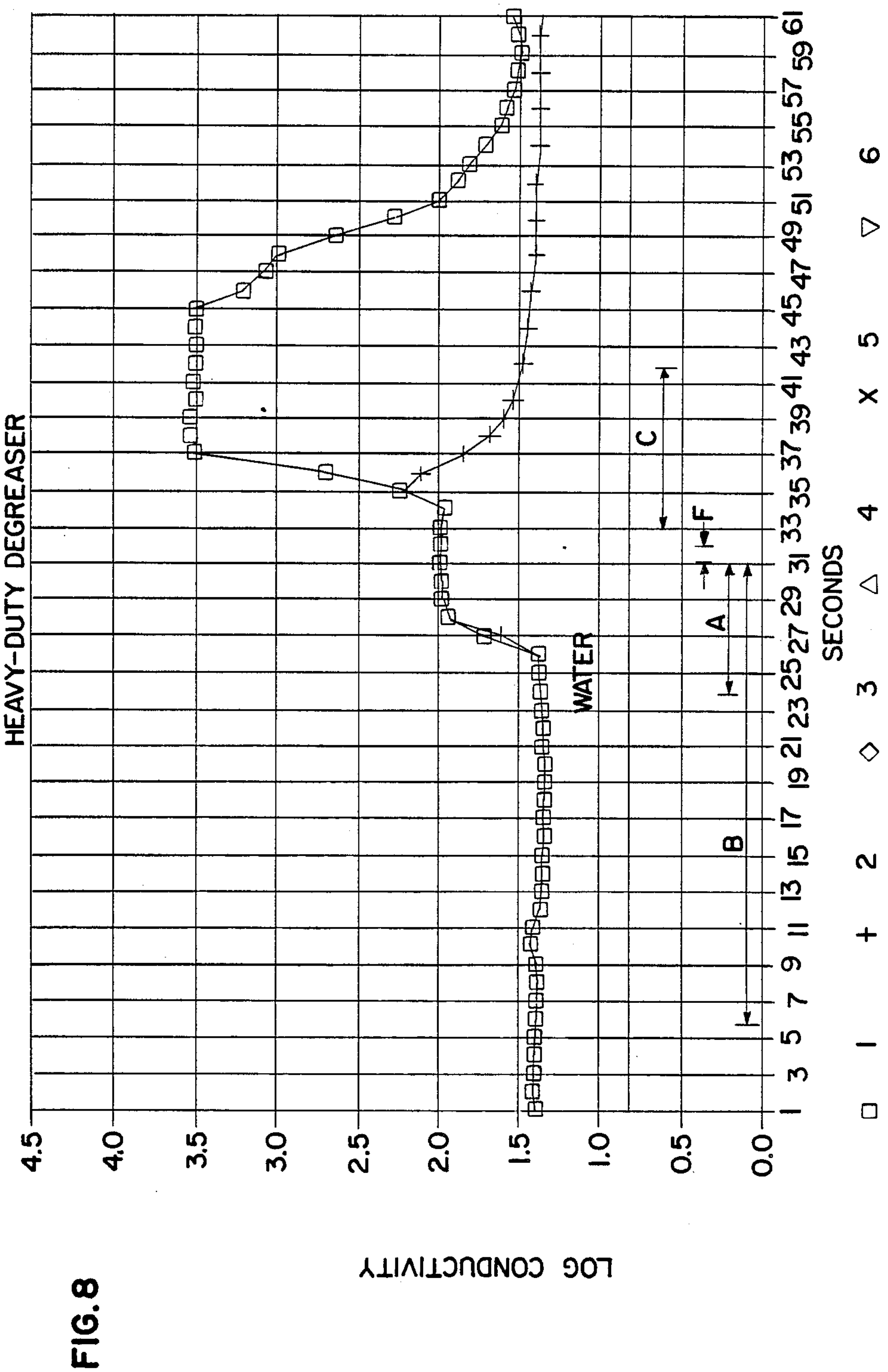
FIG. 8 is a conductivity graph for the product formulation described in Example II.

This example illustrates the production of five gallons of all-purpose cleaner. As shown in Table I (under "All Purpose Cleaner"), this cleaner utilizes three raw materials: Concentrates A, D and F. For a total of five gallons, this results in weights of 4.21 pounds of Concentrate A, 2.53 pounds of Concentrate D, 0.04 pounds of Concentrate F and 35.66 pounds of water. It is assumed that the pumping rate for Concentrate A is 8,000 mls./min.; the pumping rate for Concentrate D is 3,000 mls./min.; and the pumping rate for Concentrate F is 4,000 mls./min. When the dispensing cycle begins, water runs through the manifold 38 at a rate of four gallons per minute, and this water flow continues throughout the entire dispensing cycle. For this product, the water is run for 4281 meter counts, there being one thousand meter counts per gallon. Six seconds into the production cycle, as shown at the bottom of FIG. 7, the Concentrate F pump turns on for one second. Referring to the conductivity graph of FIG. 6, there is a conductivity spike related to Concentrate F at ten seconds on the graph. The four second delay is due to the time it takes for Concentrate F to move down the manifold 38 from its entry port 39 to the conductivity cell 50. At eight seconds into the production cycle, the Concentrate A pump is on for thirteen seconds, which is reflected in the graph of FIG. 6 by a conductivity output in a range typical for Concentrate A. At fifteen seconds into the dispensing cycle, the Concentrate D pump activates for a total of twenty-two seconds. The effect of Concentrate D, a non-ionic surfactant, on Concentrate A, an anionic surfactant, appears on the graph of FIG. 6 at the nineteen second mark. Toward the end of the dispensing cycle, after twenty-three seconds, the effect of Concentrate D alone is shown and then the effect of water alone. It should be noted that materials such as Concentrate D which do not have conductive properties nevertheless have an impact on the conductivity graph, e.g., in this example by lowering the apparent conductivity of Concentrate A. For this example, the yellow dye pump becomes activated at seven seconds into the dispensing cycle and runs for two seconds, whereas the lemon perfume pump becomes activated at eight seconds into the dispensing cycle for a period of three seconds. However, the dyes and perfumes do not have a detectable effect on the conductivity. The final fluid going through the manifold is the remaining amount of water which is regulated by the flow meter, and this final flush provides a flush of several seconds. After the dispensing cycle is complete, the full container is weighed to assure that the five gallons of all-purpose cleaner falls within the weight specification range of 42.0–43.0 pounds.

EXAMPLE II

The second example illustrates the production of a heavy-duty degreaser. This cleaner utilizes four different concentrates: Concentrate A, Concentrate B, Concentrate C, and Concentrate F. No dyes or perfumes are used for this cleaner. For a total of five gallons, this results in weights of 2.14 pounds of Concentrate A; 6.83 pounds of Concentrate B; 2.05 pounds of Concentrate C; 0.17 pounds of Concentrate F; and 31.93 pounds of water. It is assumed that the pumping rate for Concentrate A is 8,000 mls./min.; the pumping rate for Concentrate B is 6,000 mls./min.; the pumping rate for Concentrate C is 4,000 mls./min.; and the pumping rate for Concentrate F is 4,000 mls./min. Again, the dispensing cycle is initiated by the initial water flush. At six seconds into the dispensing cycle, the Concentrate B pump and corresponding valve are actuated, so as to deliver Concentrate B for twenty-five seconds. Referring to the graph of FIG. 7, it is noted that Concentrate B, a solvent blend, does not affect the conductivity in the manifold 38. After twenty-four seconds, the pump for Concentrate A starts for a run time of seven seconds, and the conductivity in the manifold 38 increases. It should be noted that conductivity at this point is two log units, while the conductivity of Concentrate A alone in the previous example was 2.25 units, the difference being the effect of Concentrate B on Concentrate A. At thirty-one seconds into the dispensing cycle, the Concentrate F pump is activated for one second. At thirty-three seconds into the dispensing cycle, the Concentrate C pump is activated for nine seconds. The graph of FIG. 7 provides an indication of how the conductivity read-out is useful for detecting malfunctioning of the pumps 43. The line indicated by squares on the graph indicate a properly made product. In contrast, the graphical output noted by x's reflected the output when the Concentrate C pump was turned off. This difference between graphical outputs enables the operator to determine that the Concentrate C pump has malfunctioned. Another quality control measure is to weigh the full, five-gallon container of the product, which for this particular example should be within the weight range of 43.07–43.62 pounds.

Although the present invention has been described with reference to one particular embodiment, it should be understood that those skilled in the art may make many other modifications without departing from the spirit and scope of the invention as defined by the appended claims.

What is claimed is:

1. An apparatus for mixing and dispensing chemical solutions, comprising:

(a) a manifold having a main passage, a plurality of chemical inlet ports connected to said passage, an outlet port connected to said passage, and a water inlet port connected to a source of pressurized water;

(b) a plurality of pumps which are selectively controllable, one of said pumps being connected to each of said chemical inlet ports so as to pump a chemical solution therethrough;

(c) selectively controllable valve means associated with each said chemical inlet ports;

(d) a dispensing outlet connected to said outlet port for dispensing said chemical solutions and water into a container; and (e) quality control means for determining whether the proper chemical solutions have been dispensed, wherein said quality control means comprises:

(i) means for repeatedly measuring the conductivity of the chemical solutions flowing through said main passage of said manifold to produce a conductivity output; and (ii) means for comparing said conductivity output with a standard conductivity output.

2. The apparatus of claim 1, wherein said quality control means comprises:

(a) means for weighing the container having the chemical solutions therein to produce a weight output; and (b) means for comparing said weight output with a standard weight range.

3. The apparatus of claim 1, wherein said quality control means comprises:

(a) means for measuring the volume of the chemical solutions flowing through said manifold outlet port to produce a volume output; and (b) means for comparing said volume output with a standard volume range.

4. The apparatus of claim 2, wherein said dispensing outlet is interconnected to selectively controllable, pneumatic position control means so as to be movable between a first, non-operative position and a second, fill position in which said dispensing outlet is located within said container.

5. The apparatus of claim 4, wherein said position control means includes means for withdrawing said dispensing outlet from the container at a first, relatively slow speed until said dispensing outlet breaks a liquid surface, and at a second, relatively fast speed thereafter.

6. The apparatus of claim 4, further comprising a drip cup assembly including:

(a) a hinged plate movable by said dispensing outlet between a first closed position and a second open position corresponding respectively to said first and second positions of said dispensing outlet;

(b) a drainage cavity having an upper end and a lower end, said plate being mounted proximate said upper end and said lower end including a drain, wherein fluid on said plate is directed into said drainage cavity.

7. The apparatus of claim 6, wherein said manifold passage has first and second ends, said plurality of chemical inlet ports being intermediate between said ends, said outlet port being at said second end and said water inlet port being at said opposite, first end of said manifold.

8. An apparatus for mixing and dispensing chemical solutions, comprising:

(a) a manifold with a first and opposite second end and having a main passage, a plurality of chemical inlet ports connected to said passage intermediate between said ends, an outlet port at said second end connected to said passage, and a water inlet port at said first end connected to a source of pressurized water;

(b) a plurality of pumps which are selectively controllable, one of said pumps being connected to each of said chemical inlet ports so as to pump a chemical solution there through;

(c) selectively controllable valve means associated with each said chemical inlet ports;

(d) a dispensing outlet connected to said outlet port for dispensing said chemical solutions and water into a container; and (e) control means operatively associated with said pumps and said valve means to operate said pumps and said valve means automatically in response to a pre-selected volume, sequential combination and concentration of chemical fluids to discharge the desired volume and combination of chemicals into said manifold.

9. The apparatus of claim 8, wherein said control means causes at least two types of chemical solutions to flow through said manifold simultaneously during a dispensing cycle.

10. The apparatus of claim 13, wherein said dispensing outlet is interconnected to selectively controllable pneumatic position control means so as to be movable between a first, non-operative position and a second fill position in which said dispensing outlet is located within said container.

11. The apparatus of claim 10, wherein said position control means includes means for withdrawing said dispensing outlet from the container at a first, relatively slow speed until said dispensing outlet breaks a liquid surface, and at a second, relatively fast speed thereafter.

12. The apparatus of claim 10, further comprising a drip cup assembly including:

(a) a hinged plate movable by said dispensing outlet between a first closed position and a second open position corresponding respectively to said first and second positions of said dispensing outlet;

(b) a drainage cavity having an upper end and a lower end, said plate being mounted proximate said upper end and said lower end including a drain, wherein fluid on said plate is directed into said drainage cavity.

13. The apparatus of claim 8, further comprising lid attachment means for securing a lid upon the container.

14. The apparatus of claim 8, wherein said valve means comprises a pneumatically-activated ball valve.

15. The apparatus of claim 8, wherein said pumps are positive displacement gear pumps.

16. The apparatus of claim 8, wherein a storage tank of concentrated liquid chemical is connected by a supply line to each of said chemical inlet ports.

17. The apparatus of claim 16, further comprising electrical sensing means associated with each storage tank for indicating to said control unit the amount of liquid chemical within said storage tank.

18. The apparatus of claim 16, further comprising a bar code reader for reading a product type bar code from a label on the product container.

19. A method of mixing and dispensing chemical solutions, comprising the steps of:

(a) positioning a dispensing outlet within a product container;

(b) pumping a plurality of concentrated chemicals from storage tanks through selectively controllable valve means by pump means connected to chemical inlet lines, through a manifold, and through said dispensing outlet;

(c) simultaneously metering a predetermined amount of water through said manifold and said distribution outlet;

(d) automatically controlling said pump means and said valve means by electronic control means in response to a pre-selected volume, sequential combination, and concentration of chemical fluid; and (e) monitoring the quality of said dispensed chemical solutions to determine whether the proper chemical solutions have been dispensed.

20. The method of claim 19, wherein at least two of said concentrated chemicals are pumped simultaneously through said manifold by said pump means.

21. The method of claim 19, wherein said quality monitoring step includes:

(a) repeatedly measuring the conductivity of the chemical solutions flowing through said manifold to produce a conductivity output; and (b) comparing said conductivity output with a standard conductivity output.

22. The method of claim 19, wherein said quality monitoring step includes:

(a) weighing the container having the chemical solutions therein to produce a weight output; and (b) comparing said weight output with a standard weight range.

23. The method of claim 19, wherein said quality monitoring step includes:

(a) measuring the volume of the chemical solutions flowing through said manifold outlet port to produce a volume output; and (b) comparing said volume output with a standard volume range.

24. The method of claim 19, further comprising the step of attaching a lid to the product container before said pumping step.

25. The method of claim 24, further comprising the step of attaching a label to the product container.

* * * * *

UNITED STATES PATENT AND TRADEMARK OFFICE

CERTIFICATE OF CORRECTION

PATENT NO. : 4,976,137

DATED : December 11, 1990

INVENTOR(S) : Decker et al

It is certified that error appears in the above-identified patent and that said Letters Patent is hereby corrected as shown below:

In the abstract, line 10, please delete "systems" and substitute therefor --system--.

In column 5, line 27, please insert --.-- after the word "speeds".

In column 7, line 3, please insert --.-- after the word "pressure".

In column 9, line 35, please delete "32" and substitute therefor --38--.

In column 13, line 10, please insert --.-- after the word "entered".

In column 6, line 19, please delete "24" and substitute therefor --25--.

UNITED STATES PATENT AND TRADEMARK OFFICE

CERTIFICATE OF CORRECTION

PATENT NO. : 4,976,137

DATED : December 11, 1990

INVENTOR(S) : Decker et al

It is certified that error appears in the above-identified patent and that said Letters Patent is hereby corrected as shown below:

In column 9, line 42, please delete "24" and substitute therefor --25--.

Signed and Sealed this

Seventh Day of July, 1992

*Attest:*

DOUGLAS B. COMER

*Attesting Officer*

*Acting Commissioner of Patents and Trademarks*